United States Patent [19]
Sprengeler et al.

[11] Patent Number: 5,612,339
[45] Date of Patent: Mar. 18, 1997

[54] 2-HYDROXY-3-AMINOPROPYLSULFON-AMIDES

[75] Inventors: Paul Sprengeler, Philadelphia; Amos B. Smith, III, Merion; Ralph F. Hirschmann, Blue Bell; Akihisa Yokoyama, Philadelphia, all of Pa.

[73] Assignee: Trustees Of The University Of Pennsylvania, Philadelphia, Pa.

[21] Appl. No.: 373,651

[22] Filed: Jan. 17, 1995

[51] Int. Cl.$^6$ ..................................... A61K 31/50
[52] U.S. Cl. ................ 514/252; 544/360; 549/552; 564/80; 564/84; 564/86; 564/95; 564/98
[58] Field of Search ............... 544/360; 549/552; 564/80, 84, 86, 95, 98; 514/252

[56] References Cited

PUBLICATIONS

Askin, D. et al., "Highly Diastereoselective Reaction of Chiral, Non–Racemic Amide Enolate with (s)–Glycidyl Toslyate. Synthesis of the Orally Active HIV–1 Protease Inhibitor L–735,524", *Tetrahedron Letters* 1994, 35, 673–676.

Cheng, Y.–S. et al., "Stability and Activity of Human Immunodeficiency Virus Protease: Comparison of the Natural Dimer with a Homologous, Single–Chain Tethered Dimer", *PNAS USA* 1990, 87, 9660–9664.

Dorsey, B. et al., "L–735,524: The Design of a Potent and Orally Bioavailable HIV Protease Inhibitor", *J. of Med. Chem.* 1994, 37(21), 3443–3451.

Gallo, R. et al., "Frequent Detection and Isolation of Cytopathic Retroviruses (HTLV–III) from Patients with AIDS and at Risk for AIDS", *Science* 1984, 224, 500–503.

Heimbach, J. et al., "Affinity Purification of the HIV–1 Protease", *Biochem. and Biophys. Res. Comm.* 1989, 164(3), 955–960.

Krohn, A. et al., "Novel Binding Mode of Highly Potent HIV–Proteinase Inhibitors Incorporating the (R)–Hydroxyethylamine Isostere", *J. Med. Chem.* 1991, 34, 3340–3342.

The Merck Index, Eleventh Edition, Budavari, et al. Eds., pp. 1403–1414, Merck & Co., Inc., New Jersey, 1989.

Miyoshi, I. et al., "Type C Virus Particles in a Cord T–Cell Line Derived by Co–Cultivating Normal Human Cord Leukocytes and Human Leukaemic T Cells", *Nature* 1981, 294, 770–771.

Popovic, M. et al., "Detection, Isolation, and Continuous Production of Cytopathic Retroviruses (HTLV–III) from Patients with AIDS and Pre–AIDS", *Science* 1984, 224, 497–500.

Roberts, N. et al., "Rational Design of Peptide–Based HIV Proteinase Inhibitors", *Science* 1990, 248, 358–361.

Sarngadharan, M. G. et al., "Antibodies Reactive with Human T–Lymphotropic Retroviruses (HTLV–III) in the Serum of Patients with AIDS", *Science* 1984, 224, 506–508.

Schupbach, J. et al., "Serological Analysis of a Subgroup of Human T–Lymphotropic Retroviruses (HTLV–III) Associated with AIDS", *Science* 1984, 224, 503–505.

Thompson, W. et al., "Synthesis and Antiviral Activity of a Series of HIV–1 Protease Inhibitors with Functionality Tethered to the $P^1$ or $P^1$, Phenyl Substituents: X–ray Crystal Structure Assisted Design", *J. Med. Chem.* 1992, 35, 1685–1701.

Zhang, Z.–Y. et al., "Dissociative Inhibition of Dimeric Enzymes", *The J. of Biol. Chem.* 1991, 266(24), 15591–15594.

*Primary Examiner*—Cecilia Tsang
*Attorney, Agent, or Firm*—Woodcock Washburn Kurtz Mackiewicz & Norris

[57] ABSTRACT

2-Hydroxy-3-aminopropylsulfonamides are provided along with methods for synthesizing and using such compounds, and chemical intermediates employed in the synthetic methods.

24 Claims, 2 Drawing Sheets

2-HYDROXY-3-AMINOPROPYLSULFONAMIDES

GOVERNMENT SUPPORT

Certain of the inventors have been supported by National Institute of General Medical Sciences Grant GM-45611.

FIELD OF THE INVENTION

This invention relates to 2-hydroxy-3-aminopropylsulfonamides, to methods for synthesizing and using such compounds, and to chemical intermediates employed in the synthetic methods.

BACKGROUND OF THE INVENTION

Depending on their use, antibacterial agents can be classified as antiseptics (agents that destroy or inhibit microorganisms when applied to living tissue) and disinfectants (agents that perform the same function but are intended for use on inanimate objects). There are a wide variety of compounds that decrease bacterial count when applied directly to a surface. Sulfonamides, for example, have a wide range of antibacterial activity. Bacterial strains, however, have become increasingly resistant to known antibacterial compounds, and the usefulness of these compounds has diminished correspondingly. Accordingly, there remains a need in the art for novel antibacterial agents to which commonly-encountered bacteria are not resistant.

OBJECTS OF THE INVENTION

It is one object of the present invention to provide novel antibacterial agents.

It is a further object of the invention to provide novel 2-hydroxy-3-aminopropylsulfonamides.

It is another object to provide methods for synthesizing 2-hydroxy-3-aminopropylsulfonamides.

It is yet another object to provide chemical intermediates employed in the synthetic methods.

It is a further object to provide antibacterial compositions comprising 2-hydroxy-3-aminopropylsulfonamides.

It is yet another object to provide methods for inactivating bacteria by contacting the bacteria with a 2-hydroxy-3-aminopropylsulfonamides of the invention.

SUMMARY OF THE INVENTION

These and other objects are accomplished by the present invention, which provides 2-hydroxy-3-aminopropylsulfonamides having formulas I and II:

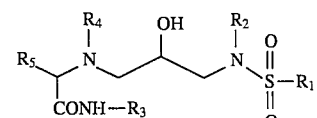

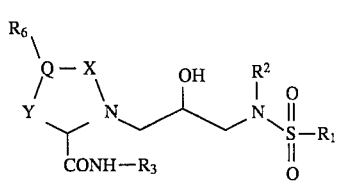

wherein:

$R_1$ is H, OH, alkyl having 1 to about 10 carbon atoms, or aryl having 3 to about 20 carbon atoms;

$R_2$ is H, alkyl having 1 to about 10 carbon atoms, aryl having 3 to about 20 carbon atoms, alkaryl having 4 to about 25 carbon atoms, or an amino acid side chain;

$R_3$ is H, alkyl having one to about 10 carbon atoms, or alkaryl having 4 to about 25 carbon atoms;

$R_4$ is H, alkyl having 1 to about 10 carbon atoms, aryl having 3 to about 20 carbon atoms, alkaryl having 4 to about 25 carbon atoms, or an amino acid side chain;

$R_5$ is H, alkyl having one to about 10 carbon atoms, or aryl having 3 to about 20 carbon atoms;

$R_6$ is H, alkyl having one to about 10 carbon atoms, aryl having 3 to about 20 carbon atoms, or alkaryl having 4 to about 25 carbon atoms;

X and Y are, independently, alkylene having 1 to about 6 carbon atoms, provided that the sum of X and Y is less than or equal to 9; and Q is N or $CH_2$.

In another aspect, the invention provides synthetic intermediates that can be used to prepare sulfonamides having structures I and II. One preferred class of synthetic intermediates has formula III:

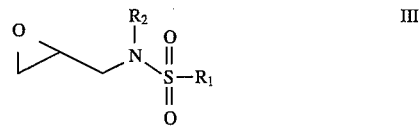

wherein $R_1$ and $R_2$ are as defined above.

The invention also provides compositions containing the compounds of the invention, and methods for inactivating bacteria by contacting the bacteria (or an object suspected to bear the bacteria) with a compound or composition of the invention.

BRIEF DESCRIPTION OF THE FIGURES

The numerous objects and advantages of the present invention can be better understood by those skilled in the art by reference to the accompanying figures, in which.

DETAILED DESCRIPTION OF THE INVENTION

Figure 1:
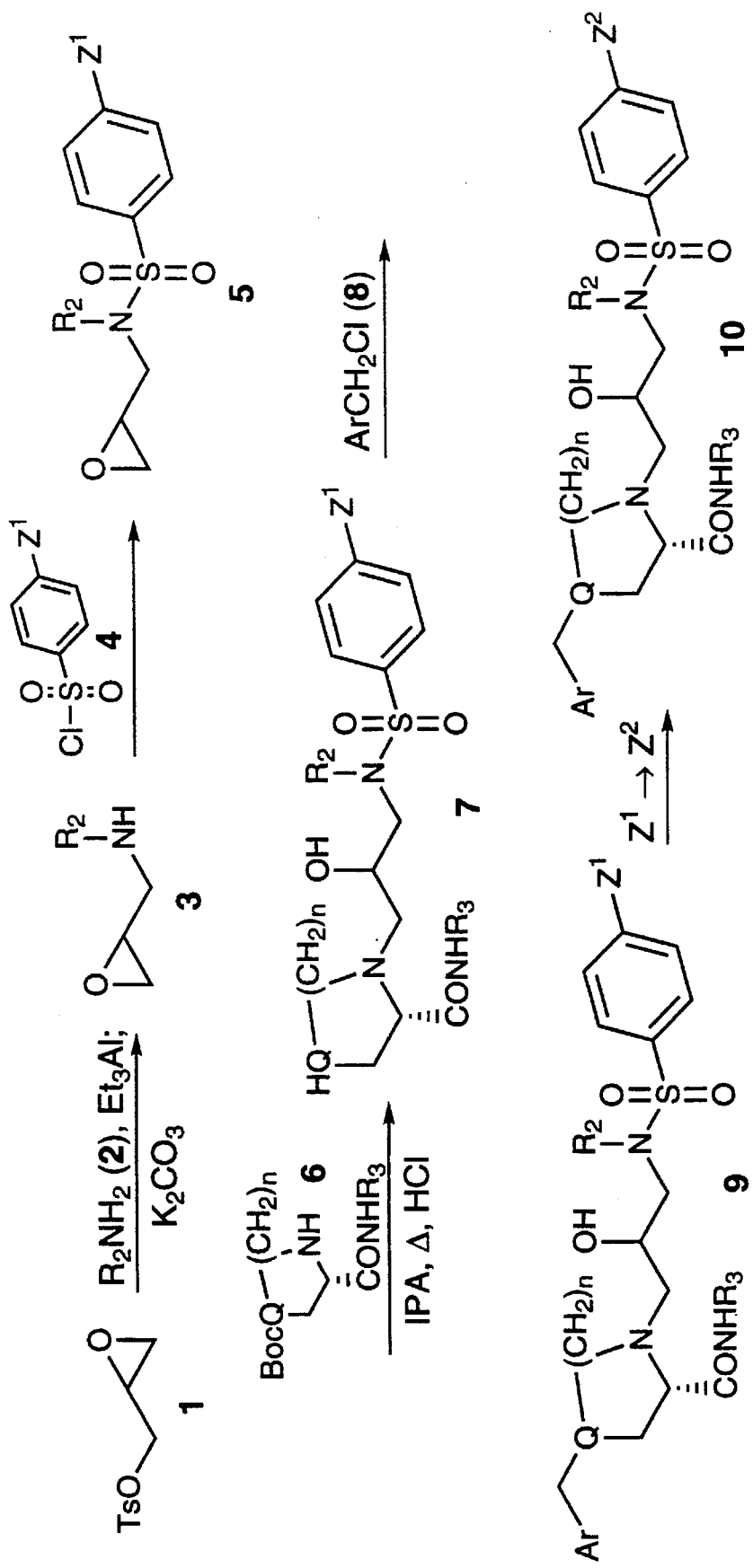
FIG. 1 shows a synthetic scheme for compounds having formula (10).

This invention provides a new class of sulfonamide-containing compounds. According to certain embodiments of the invention, somewhat linear compounds are provided having formula I:

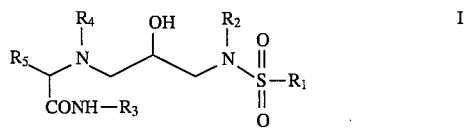

wherein:

$R_1$ is H, OH, alkyl having 1 to about 10 carbon atoms, or aryl having 3 to about 20 carbon atoms;

$R_2$ is H, alkyl having 1 to about 10 carbon atoms, aryl having 3 to about 20 carbon atoms, alkaryl having 4 to about 25 carbon atoms, or an amino acid side chain;

$R_3$ is H, alkyl having one to about 10 carbon atoms, or alkaryl having 4 to about 25 carbon atoms;

$R_4$ is H, alkyl having 1 to about 10 carbon atoms, aryl having 3 to about 20 carbon atoms, alkaryl having 4 to about 25 carbon atoms, or an amino acid side chain;

$R_5$ is H, alkyl having one to about 10 carbon atoms, or aryl having 3 to about 20 carbon atoms.

According to other embodiments, somewhat cyclic compounds are provided having formula II:

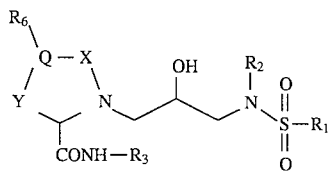

wherein $R_1$, $R_2$, $R_3$, $R_4$, and $R_5$ are as defined above and:

$R_6$ is H, alkyl having one to about 10 carbon atoms, aryl having 3 to about 20 carbon atoms, or alkaryl having 4 to about 25 carbon atoms;

X and Y are, independently, alkylene having 1 to about 6 carbon atoms, provided that the sum of X and Y is less than or equal to 9; and Q is N or $CH_2$.

Alkyl groups according to the invention include but are not limited to straight chain, branched chain, and cyclic hydrocarbons such as methyl, ethyl, propyl, pentyl, isopropyl, 2-butyl, isobutyl, 2-methylbutyl, and isopentyl moieties having 1 to about 10 carbon atoms, preferably 1 to about 6 carbon atoms. Alkylene groups according to the invention are straight chain or branched chain hydrocarbons that are covalently bound to two other groups. Preferred alkylene groups have the formula —$(CH_2)_n$— where n is 1 to about 6, preferably 1 to about 3, including methylene (n=1) and ethylene (n=2) groups.

Aryl groups according to the invention are aromatic groups having 3 to about 20 carbon atoms, preferably from 3 to about 10 carbon atoms, including, for example, imidazolyl, naphthyl, phenyl, pyridyl, pyrimidinyl, and xylyl groups and substituted derivatives thereof, particularly those substituted with amino, nitro, hydroxy, methyl, methoxy, thiomethyl, trifluoromethyl, mercaptyl, and carboxy groups. One preferred point for substitution is position Z shown in FIG. 1. Alkaryl groups are groups that contain alkyl and aryl portions and are covalently bound to other groups through the alkyl portion, as in a benzyl group.

The term amino acid as used herein is intended to include all naturally-occurring and synthetic amino acids known in the art. In general, amino acids have structure $H_2N$—$CH(R_c)$—$C(O)OH$ where $R_c$ is the amino acid side chain. Representative, naturally-occurring side chains are shown in Table 1.

TABLE 1

| | |
|---|---|
| $CH_3$— | $CH_3$—$CH_2$—S—$CH_2$—$CH_2$— |
| HO—$CH_2$— | HO—$CH_2$—$CH_2$— |
| $C_6H_5$—$CH_2$— | $CH_3$—$CH_2(OH)$— |
| HO—$C_6H_5$—$CH_2$— | $HO_2C$—$CH_2$—$NH_2C(O)$—$CH_2$— |
| HO—⟨phenyl⟩—$CH_2$—, HO | ⟨azetidinyl NH⟩ |
| ⟨indolyl⟩—$CH_2$— | $HCO_2$—$CH_2$—$CH_2$—<br>$NH_2C(O)$—$CH_2$—$CH_2$—<br>$(CH_3)_2$—CH—<br>$(CH_3)_2$—CH—$CH_2$—<br>$CH_3$—$CH_2$—$CH_2$— |
| ⟨imidazolyl⟩—$CH_2$— | $H_2N$—$CH_2$—$CH_2$—$CH_2$—<br>$H_2N$—C(NH)—NH—$CH_2$—$CH_2$—$CH_2$—<br>$H_2N$—C(O)—NH—$CH_2$—$CH_2$—$CH_2$—<br>$CH_3$—$CH_2$—$CH(CH_3)$— |
| HS—$CH_2$—<br>$HO_2C$—$CH(NH_2)$—$CH_2$—S—S—$CH_2$—<br>$CH_3$—$CH_2$—<br>$CH_3$—S—$CH_2$—$CH_2$— | $CH_3$—$CH_2$—$CH_2$—$CH_2$—<br>$H_2N$—$CH_2$—$CH_2$—$CH_2$—$CH_2$— |

Preferred side chains include $(CH_3)_2$—CH—, $(CH_3)_2$—CH—$CH_2$—, $C_6H_5$—$CH_2$—, and $R_jC(O)C(O)$—$(CH_2)_z$—O—$C_6H_5$—$CH_2$— where z is 1 to about 10 (preferably 1–6) and $R_j$ is H or alkyl having 1 to about 12 carbon atoms.

The sulfonamides of the invention contain amino groups and, therefore, are capable of forming salts with various inorganic and organic acids. Such salts are also within the scope of this invention. Representative salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, sulfate, tartrate, rosylate, and undecanoate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

In one aspect, the present invention provides antibacterial compositions comprising one or more sulfonamide compounds, as well as methods for inactivating (e.g., killing) bacteria by contacting them with a compound according to the invention or a composition comprising a compound according to the invention. The compositions of the invention include one or more of sulfonamide compounds as an active ingredient in admixture with a suitable organic or inorganic carrier or excipient. One anticipated use of the claimed compounds involves inactivating bacteria suspected to be borne on food preparation surfaces or other objects by contacting such objects with a composition of the invention. Solutions containing sulfonamide compounds are prepared for such uses by dissolving the sulfonamide in a suitable (preferably volatile) organic solvent such as methanol, ethanol, propanol, dimethylsulfoxide, ethyl ether, dimethylformamide, tetrahydrofuran, acetonitrile, petroleum ether, hexanes, benzene, methylene chloride, chloroform, carbon tetrachloride, and pyridine. Aqueous solutions are prepared by dissolving the sulfonamide or its salt (and, optionally, a surfactant) in water or some other aqueous medium. Surfactants according to the invention are compounds that modify the surface tension of the aqueous system and facilitate dissolution of the sulfonamide and/or its salt. Sulfonamides also can be compounded, for example, with the usual non-toxic, pharmaceutically acceptable carriers for tablets, pellets, capsules, suppositories, solutions, emulsions, suspensions, and any other form suitable for therapeutic use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes maybe used. The active ingredient is included in the composition in an amount sufficient to produce the desired antibacterial or antimicrobial effect.

Additional objects, advantages, and novel features of this invention will become apparent to those skilled in the art upon examination of the following examples thereof, which are not intended to be limiting.

EXAMPLE 1

GENERAL SYNTHESIS OF COMPOUNDS HAVING FORMULA (10)

A. (S)- or (R)- N-Glycidyl N-alkylamine (3)

As shown in FIG. 1, to a stirred solution of alkylamine (2) (5.0 mmol) and dichloromethane (15 mL) under argon is added triethylaluminum (3.2 mL, 1.55M in toluene) dropwise over about 5 minutes. (R)- or (S)-Glycidyl tosylate (1) (5.0 mmol) is added after 30 minutes and the reaction mixture is allowed to stir overnight at room temperature. After carefully quenching the reaction mixture by dropwise addition of 6M sodium hydroxide (4 mL) the mixture is stirred for about 1–2 hours. The layers are separated and the aqueous phase is extracted with dichloromethane, dried over sodium sulfate, and concentrated in vacuo. The residue is dissolved in dry methanol (100 mL) and anhydrous potassium carbonate (3.1 g, 22 mmol) is added at room temperature. The mixture is stirred for 3 hours, poured into brine (500 mL), and the aqueous layer is extracted with chloroform (3 x). The dried residue is purified via flash chromatography to afford (S)- or (R)-N-glycidyl N-alkylamine (3).

B. (S)- or (R)-N-Glycidyl N-alkyl-4-$Z^1$-benzene-sulfonamide (5)

To (S)- or (R) -N-glycidyl N-alkylamine (3) (5 mmol) in pyridine (50 mL) at 55°–65° C. is added slowly 4-$Z^1$-benzene-sulfonyl chloride (4) (5.1 mmol). The mixture is allowed to stir for 4–6 hours at 55°–65° C. and the pyridine is then removed in vacuo and the residue purified by flash chromatography to afford (S)-or (R)-N-glycidyl N-alkyl-4-$Z^1$-benzenesulfonamide (5).

C. 2(S)- or 2(R)-1-[N-Alkyl-N-(4-$Z^1$-benzene-sulfonyl)amino]-3-[1-[2(S)-(N-tert-butylcarbamoyl)aminocyclic]-2-propanol (7)

(S)- or (R)-N-Glycidyl N-alkyl-4-$Z^1$-benzenesulfonamide (5) (5 mmol) and N-tert-butyl-4-[(1,1-dimethylethoxy) carbonyl]aminocyclic-2(S) -carboxamide (6) (5.4 mmol) are dissolved in isopropanol (100 mL) and allowed to stir at 85° C. for 60 hours. The mixture is concentrated in vacuo and the residue (if necessary) is dissolved in isopropanol (35 mL) and treated with 6N HCl (40 mL) at 0° C. for 1 hour. The mixture is stirred an additional 6 hours at room temperature, cooled to 0° C., carefully quenched with 5 N NaOH until pH 10, and partitioned between ethyl acetate and water. The aqueous phase is extracted with ethyl acetate and the combined organic phases washed with water and brine, dried over magnesium sulfate, concentrated in vacuo, and purified by flash chromatography to afford 2(S)- or 2(R)-1-[N-alkyl-N-(4-$Z^1$-benzenesulfonyl)amino]-3-[1-[2(S)-(N-tert-butylcarbamoyl)aminocyclic]]-2-propanol (7)

D. 2(S)- or 2(R)-1-[N-Alkyl-N-(4-$Z^1$-benzene-sulfonyl)amino]-3-[1-[4-(arylmethyl)-2(S)-(N-tert-butylcarbamoyl) aminocyclic]]-2-propanol (9)

To 2(S)- or 2(R)-1-[N-alkyl-N-(4-$Z^1$-benzenesulfonyl)amino]-3-[1-[2(S)-(N-tert-butylcarbamoyl)aminocyclic]]-2-propanol (7) (5 mmol) in DMF (10.5 mL) is added arylmethyl chloride (8) (Ar=aryl group; 5.5 mmol) and triethylamine (1.54 mL, 11 mmol). After 12 hours, the reaction mixture is diluted with ethyl acetate (100 mL) washed with water and brine, dried over magnesium sulfate, concentrated in vacuo, and purified by flash chromatography to afford 2(S)- or 2(R)-1-[N-alkyl-N-(4-$Z^1$-benzenesulfonyl)amino]-3-[1-[4-(arylmethyl)-2(S)-(N-tert-butylcarbamoyl)aminocyclic]]-2-propanol (9).

E. 2(S)- or 2 (R)-1-[N-Alkyl-N-(4-$Z^3$-benzene-sulfonyl)amino]-3-[1-[4-(arylmethyl)-2(S)- (N-tert-butylcarbamoyl) aminocyclic]]-2-propanol (10)

The protecting group on the benzenesulfonyl moiety of 2(S) - or 2(R)-1-[N-Alkyl-N-(4-$Z^1$-benzenesulfonyl) amino] -3-[1-[4-(arylmethyl)-2(S) -(N-tert-butylcarbamoyl)aminocyclic]]-2-propanol (9) is deprotected (if necessary) using standard procedures to afford 2 (S) - or 2 (R)-1-[N-alkyl-N-(4-$Z^3$-benzene-sulfonyl)amino]-3-[1-[4-(arylmethyl)-2(S)- (N-tert-butylcarbamoyl) aminocyclic]]-2-propanol (10).

EXAMPLE 2

SPECIFIC SYNTHESIS OF DIASTEREOMERS HAVING FORMULA (19)

A. N-iso-Butyl-allylamine (11)

Figure 2:
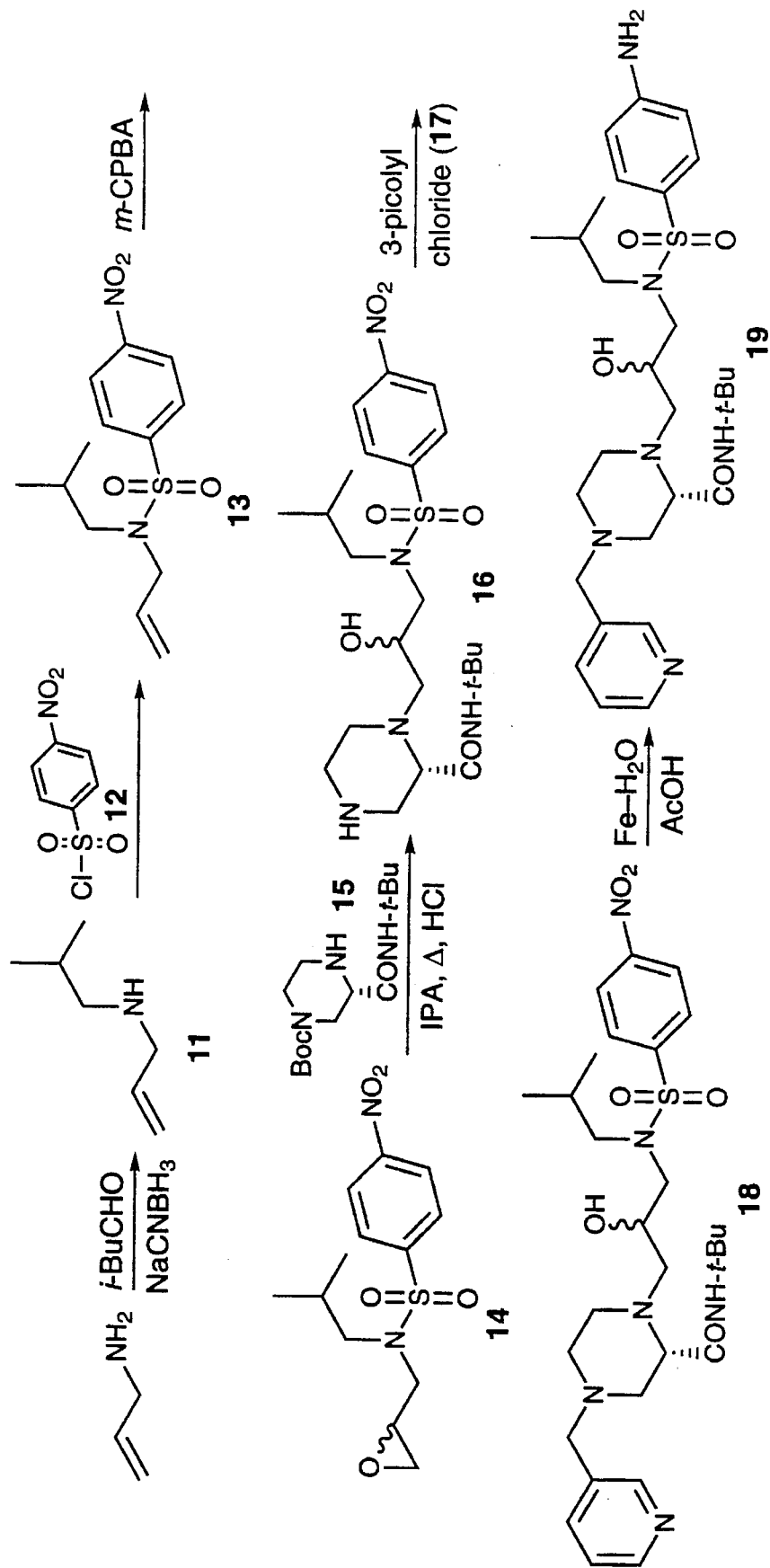
FIG. 2 shows a synthetic scheme for compounds having formula (19).

As shown in FIG. 2, to allylamine (5 mmol) in methyl alcohol (30 mL) at room temperature is added sodium cyanoborohydride (3.6 mg, 5.6 mmol). After stirring for 10 minutes, isobutyraldehyde (5 mmol) is added and the mixture is stirred for an additional 72 hours. Filtration and washing with methyl alcohol and ethyl ether is followed by drying with magnesium sulfate, concentration in vacuo, and purification by flash chromatography to affords N-iso-butyl-allylamine (11).

B. N-Allyl-N-iso-butyl-4-nitrobenzenesulfonamide (13).

To N-iso-Butyl-allylamine (11) (5 mmol) in pyridine (50 mL) at 55°–65° C. is added slowly 4-nitrobenzenesulfonyl chloride (12) (5.1 mmol). The mixture is allowed to stir for 4–6 hours at 55°–65° C. and the pyridine is then removed in vacuo and the residue purified by flash chromatography to afford N-allyl-N-iso-butyl-4-nitrobenzenesulfonamide (13).

C. N-iso-Butyl-N-2(S)- and 2(R)-glycidyl-4-nitrobenzenesulfonamide (14).

To N-allyl-N-iso-butyl-4-nitrobenzenesulfonamide (13) (5 mmol) in dichloromethane (7 mL) is added sodium bicarbonate (2.0 g, 22 mmol). Upon stirring at room temperature for 5 minutes, meta-chloroperbenzoic acid (2.0 g, 22 mmol) is added and heated at reflux for 24 hours. The mixture is poured into saturated aqueous sodium sulfite (7 mL) and the aqueous layer is extracted with ethyl ether. The combined organic layers are dried over magnesium sulfate, concentrated in vacuo, and purified by flash chromatography to afford N-iso-butyl-N-2(S)-and 2(R)-glycidyl-4-nitrobenzenesulfonamide (14).

D. 2 (S)- and 2(R)-1-[N-iso-Butyl-N-(4-nitrobenzenesulfonyl) amino]-3-[1-[2(S) -(N-tert-butylcarbamoyl)piperazinyl]]-2-propanol (16)

N-iso-Butyl-N-2(S) - and 2(R) -glycidyl-4-nitrobenzenesulfonamide (14) (5 mmol) and N-tert-butyl-4-[(1,1-dimethylethoxy) carbonyl]piperazine-2(S) -carboxamide (15) (5.4 mmol) are dissolved in isopropanol (100 mL) and allowed to stir at 85° C. for 60 hours. The mixture is concentrated in vacuo and the residue is dissolved in isopropanol (35 mL) and treated with 6N HCl (40 mL) at 0° C. for 1 hour. The mixture is stirred an additional 6 hours at room temperature, cooled to 0° C., carefully quenched with 5 N NaOH until pH 10, and partitioned between ethyl acetate and water. The aqueous phase is extracted with ethyl acetate and the combined organic phases washed with water and brine, dried over magnesium sulfate, concentrated in vacuo, and purified by flash chromatography to afford 2(S) - and 2(R)-1-[N-iso-butyl-N-(4-nitrobenzenesulfonyl) amino]-3-[1-[2(S) -(N-tert-butylcarbamoyl)piperazinyl]]-2-propanol (16).

E. 2(S) - and 2(R)-1-[N-iso-Butyl-N-(4-nitrobenzenesulfonyl) amino]-3-[1-[4-(3-pyridylmethyl)-2(S) -(N-tert-butyl carbamoyl) piperazinyl]]-2-propanol (18)

To 2(S) - and 2(R)-1-[N-iso-butyl-N-(4-nitrobenzenesulfonyl) amino]-3-[1-[2(S) - (N-tert-butylcarbamoyl)piperazinyl]]-2-propanol (16) (5 mmol) in DMF (10.5 mL) is added 3-picolyl chloride hydrochloride salt (17) (907 mg, 5.5 mmol) and triethylamine (1.54 mL, 11 mmol). After 12 hours, the reaction mixture is diluted with ethyl acetate (100 mL) washed with water and brine, dried over magnesium sulfate, concentrated in vacuo, and purified by flash chromatography to afford 2(S) - and 2(R)-1-[N-iso-butyl-N-(4-nitrobenzenesulfonyl) amino]-3-[1-[4-(3-pyridylmethyl)-2(S) -(N-tert-butyl carbamoyl) piperazinyl]]-2-propanol (18).

F. 2(S) - and 2(R)-1-[N-iso-Butyl-N-(4-sulfanilyl) amino]-3-[1-[4-(3-pyridylmethyl)-2(S)-(N-tert-butylcarbamoyl) piperazinyl]]-2-propanol (19)

To Fe-H$_2$O suspension containing a trace of acetic acid is added 2(S) - and 2(R)-1-[N-iso-butyl-N-(4-nitrobenzenesulfonyl) amino]-3-[1-[4-(3-pyridylmethyl)-2(S) -(N-tert-butyl carbamoyl) piperazinyl]]-2-propanol (18). The mixture is diluted with an equal volume of ethyl alcohol and excess ammonium hydroxide and subsequently filtered. The filtrate is concentrated in vacuo and acidified with acetic acid to pH 6 followed by purification by flash chromatography to afford 2(S) - and 2(R)-1-[N-iso-butyl-N-(4-sulfanilyl)amino]-3-[1-[4- (3-pyridylmethyl)-2(S) - (N-tert-butylcarbamoyl)piperazinyl]]-2-propanol (19).

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having formula I or II:

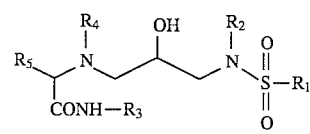

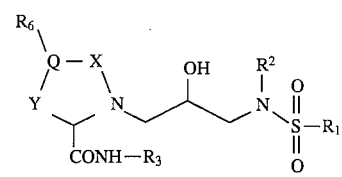

wherein:

$R_1$ is H, OH, alkyl having 1 to 10 carbon atoms, or aryl having 3 to 20 carbon atoms;

$R_2$ is H, alkyl having 1 to 10 carbon atoms, aryl having 3 to 20 carbon atoms, alkaryl having 4 to 25 carbon atoms, or an amino acid side chain;

$R_3$ is H, alkyl having one to 10 carbon atoms, or alkaryl having 4 to 25 carbon atoms;

$R_4$ is H, alkyl having 1 to 10 carbon atoms, aryl having 3 to 20 carbon atoms, alkaryl having 4 to 25 carbon atoms, or an amino acid side chain;

$R_5$ is H, alkyl having 1 to 10 carbon atoms, or aryl having 3 to 20 carbon atoms;

$R^6$ is H, alkyl having 1 to 10 carbon atoms, aryl having 3 to 20 carbon atoms, or alkaryl having 4 to 25 carbon atoms;

X and Y are, independently, alkylene having 1 to about 6 carbon atoms, provided that the sum of X and Y is less than or equal to 9;

Q is N or CH$_2$;

said amino acid side chains are independently selected from the group consisting of:

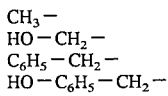
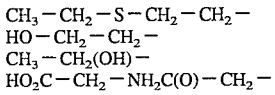
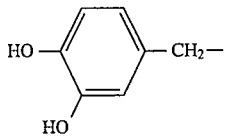
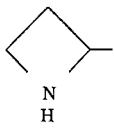
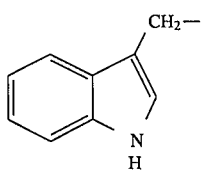
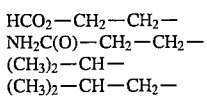
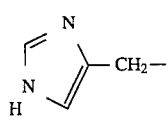
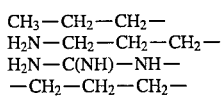
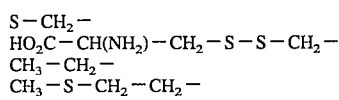
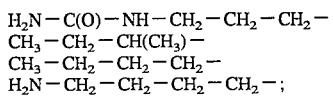

said alkyl groups are straight or branched chain groups; and said aryl groups are selected from the group consisting of imidazolyl, naphthyl, phenyl, pyridyl, pyrimidinyl, and xylyl groups optionally substituted with amino, nitro, hydroxy, methyl, methoxy, thiomethyl, trifluoromethyl, mercaptyl, and carboxy groups.

2. The compound of claim 1 wherein R$_1$ is aryl.
3. The compound of claim 1 wherein R$_1$ is aminophenyl.
4. The compound of claim 1 wherein R$_2$ is alkyl.
5. The compound of claim 1 wherein R$_2$ is isopropyl.
6. The compound of claim 1 wherein R$_3$ is t-butyl.
7. The compound of claim 1 wherein X and Y are, independently, alkylene having 1 to about 3 carbon atoms.
8. The compound of claim 1 wherein X is ethylene.
9. The compound of claim 1 wherein Y is methylene.
10. The compound of claim 1 wherein Q is N.
11. The compound of claim 1 wherein R$_6$ is alkaryl.
12. The compound of claim 1 wherein R$_6$ is picolyl.
13. The compound of claim 1 wherein R$_1$ is aryl, R$_2$ is alkyl, R$_3$ is alkyl, X and Y are, independently, alkylene having 1 to about 3 carbon atoms, Q is N, and R$_6$ is alkaryl.
14. The compound of claim 1 having structure:

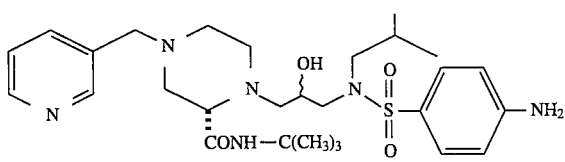

15. A method for treating an object suspected to bear bacteria, comprising contacting said object with at least one compound according to claim 1.

16. A method for inactivating bacteria comprising contacting said bacteria with at least one compound according to claim 1.

17. A composition comprising at least one compound of claim 1 in admixture with a carrier, adjuvant, or vehicle.

18. A composition comprising at least one compound of claim 1 dissolved in a solvent.

19. The composition of claim 18 wherein said solvent is an organic solvent selected from methanol, ethanol, propanol, dimethylsulfoxide, ethyl ether, dimethylformamide, tetrahydrofuran, acetonitrile, petroleum ether, hexanes, benzene, methylene chloride, chloroform, carbon tetrachloride, and pyridine.

20. The composition of claim 18 wherein said solvent is water.

21. A compound having formula:

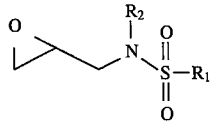

wherein:

R$_1$ is H, OH, alkyl having 1 to 10 carbon atoms, or aryl having 3 to 20 carbon atoms;

R$_2$ is H, alkyl having 1 to 10 carbon atoms, aryl having 3 to 20 carbon atoms, alkaryl having 4 to 25 carbon atoms, or an amino acid side chain selected from the group consisting of:

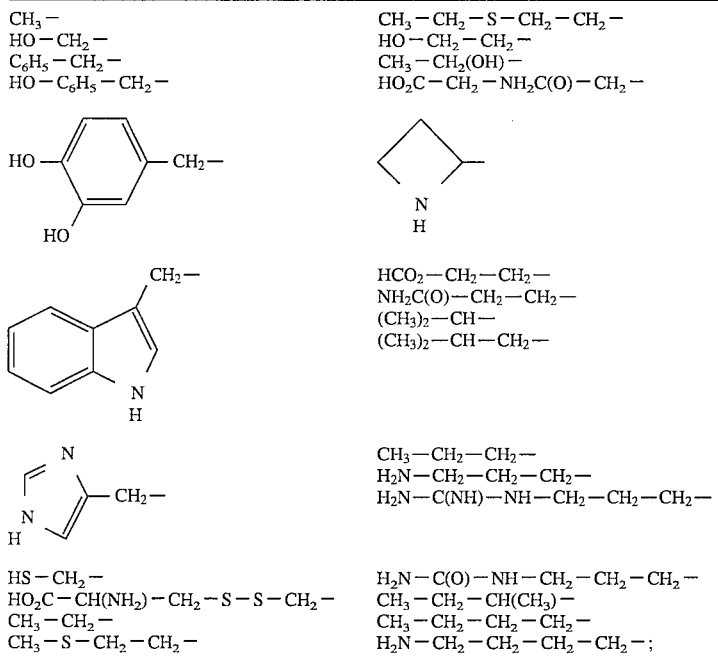

said alkyl groups are straight or branched chain groups; and said aryl groups are selected from the group consisting of imidazolyl, naphthyl, phenyl, pyridyl, pyrimidinyl, and xylyl groups optionally substituted with amino, nitro, hydroxy, methyl, methoxy, thiomethyl, trifluoromethyl, mercaptyl, and carboxy groups.

22. The compound of claim 21 wherein $R_1$ is nitrophenyl.
23. The compound of claim 21 wherein $R_2$ is isopropyl.
24. A compound having formula:

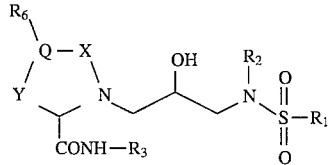

II wherein $R_1$ is aminophenyl;

$R_2$ is straight or branched chain alkyl having 1 to 10 carbon atoms;

$R_3$ is straight or branched chain alkyl having 1 to 10 carbon atoms;

$R_6$ is picolyl;

X and Y are, alkylene having 1 to 3 carbon atoms; and

Q is N.

* * * * *